(12) United States Patent
Tada et al.

(10) Patent No.: US 9,040,251 B2
(45) Date of Patent: May 26, 2015

(54) BIOMOLECULE FIXING BOARD AND METHOD OF MANUFACTURING THE SAME

(75) Inventors: Yasuhiko Tada, Tokai (JP); Hiroshi Yoshida, Mito (JP); Toshiro Saito, Hitachinaka (JP); Masatoshi Narahara, Hitachinaka (JP); Hiroaki Nakagawa, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 5 days.

(21) Appl. No.: 13/388,671

(22) PCT Filed: Jul. 29, 2010

(86) PCT No.: PCT/JP2010/062757
§ 371 (c)(1),
(2), (4) Date: Feb. 3, 2012

(87) PCT Pub. No.: WO2011/016382
PCT Pub. Date: Feb. 10, 2011

(65) Prior Publication Data
US 2012/0130050 A1    May 24, 2012

(30) Foreign Application Priority Data
Aug. 4, 2009  (JP) .................. 2009-181743

(51) Int. Cl.
*G01N 33/53* (2006.01)
*C07K 1/04* (2006.01)
*G01N 33/551* (2006.01)
*G01N 33/543* (2006.01)
*A61K 39/00* (2006.01)

(52) U.S. Cl.
CPC ........ *G01N 33/54353* (2013.01); *G01N 33/543* (2013.01); *A61K 2039/625* (2013.01); *G01N 33/54393* (2013.01)

(58) Field of Classification Search
CPC .......... G01N 33/54353; G01N 33/552; G01N 33/50; C12Q 2563/131; B01J 2219/00632
See application file for complete search history.

(56) References Cited

U.S. PATENT DOCUMENTS

| | | | |
|---|---|---|---|
| 6,787,308 | B2 | 9/2004 | Balasubramanian et al. |
| 2002/0095073 | A1 | 7/2002 | Jacobs et al. |
| 2008/0064023 | A1 | 3/2008 | Hah et al. |

FOREIGN PATENT DOCUMENTS

| | | |
|---|---|---|
| JP | 2002-520621 | 7/2002 |
| JP | 2002-365294 | 12/2002 |
| JP | 2003-517607 | 5/2003 |
| JP | 2006-522936 | 10/2006 |
| JP | 2007-298523 | 11/2007 |
| JP | 2008-180711 | 8/2008 |
| WO | WO 00/04390 A2 | 1/2000 |
| WO | WO 01/44805 A2 | 6/2001 |
| WO | WO 2004/095025 A1 | 11/2004 |

OTHER PUBLICATIONS

Wilchek et al. Introduction to Avidin-Biotin technology. Methods in Enzymology, 1990, vol. 84, pp. 5-13.*
Miura et al. The self-assembled monolayer of saccharide via click chemistry: formation and protein recognition. The solid Films 1008, vol. 516, pp. 2443-2449.*
Sun et al. Carbohydrate and protein immobilization onto solid surfaces by sequential diels-alder and azide-alkyne cycloadditions. Bioconjugate Chem. 2006, vol. 17, pp. 52-57.*
Marie et al. Generic surface modificaiton strategy for sensing applications based on Au/SiO2 nanostructures. Biointerphases 2007, vol. 2, No. 1, pp. 49-55.*
Li, Xiaosong. Synthesis of novel silanes with functional head groups, surface modificaitons, and characterizaiton. Doctoral Dissertation, Zur Erlangung des akademischen Grades, Johannes Gutenberg-Universitat Mainz, 2008, pp. 1-124.*
Lummerstorfer et al. Click chemistry on surfaces: 1,3-dipolar cycloaddition reaction of azide-terminated monolayers on silica, J. Phys. Chem. B 2004, vol. 108, pp. 3963-3966.*
Vijayendran et al. A quantitative assessment of heterogeneity for surface-immobilized proteins. Anal. Chem. 2001, vol. 73, pp. 471-480.*
Ido Braslavsky et al., Sequence information can be obtained from single DNA molecules, PNAS, Apr. 1, 2003, pp. 3960-3964, vol. 100, No. 7.
Joanna Malicka et al., DNA hybridization assays using metal-enhanced fluorescence, Biochemical and Biophysical Research Communications 306, 2003, pp. 213-218.
P. Hubert Mutin et al., Selective Surface Modification of $SiO_2$-$TiO_2$ Supports with Phosphonic Acids, American Chem. Mater. 2004, pp. 5670-5675, vol. 16, No. 26.

* cited by examiner

*Primary Examiner* — Shafiqul Haq
(74) *Attorney, Agent, or Firm* — Baker Botts L.L.P.

(57) ABSTRACT

This invention provides a biomolecule modifying substrate comprising biomolecules selectively fixed to given regions thereon. The biomolecule modifying substrate comprises: a substrate at least comprising a first surface and a second surface; a first linker molecule comprising a hydrocarbon chain and a functional group capable of selectively binding to the first surface at one end of the hydrocarbon chain, which is bound to the first surface via such functional group; a second linker molecule comprising a reactive group capable of binding to the hydrocarbon chain of the first linker molecule, which is bound to the first linker molecule via a bond between the reactive group and the hydrocarbon chain; and a biomolecule bound thereto via the second linker molecule.

8 Claims, 8 Drawing Sheets

(a) Plan view (b) Cross-sectional view (a) Plan view (b) Cross-sectional view (a) Plan view (b) Cross-sectional view (a)

(b)

(c)

(d)

(e)

(a)

(b)

(a)

(b)

BIOMOLECULE FIXING BOARD AND METHOD OF MANUFACTURING THE SAME

TECHNICAL FIELD

The present invention relates to a biomolecule modifying substrate on which biomolecules have been fixed in given regions via linker molecules and a method of manufacturing the same.

BACKGROUND ART

In recent years, human genome DNA mapping has been substantially completed, and research aimed at elucidation of gene functions has been actively conducted. It is necessary to specifically and extensively detect genes and proteins in vivo, and development of techniques for gene and protein detection has made progress worldwide. Meanwhile, a technique of identifying pathogens or viruses that have entered into organisms at the gene or protein level has heretofore been examined, and practical application of such technique has become possible. A variety of biosensors have been used as means for detecting biomolecules such as given genes or proteins in accordance with the intended purpose. The most common type of biosensor comprises a probe molecule that reduces the size of a biomolecule fixed to a solid surface. When a nucleic acid is to be captured, a nucleic acid is mainly used as a probe molecule. When a protein is to be captured, a protein is mainly used as a probe molecule. A biosensor comprising probe molecules fixed to a substrate is advantageous in that various types of probe molecules can be fixed to the same substrate via spotting system, ink-jet system, or other means. With the use of a biosensor substrate of such type, various biomolecules can be simultaneously subjected to extensive analysis, and such analysis can be completed rapidly. Representative examples of biosensors utilizing substrate surfaces include biomolecule-detecting elements, such as DNA microarrays or protein chips.

In recent years, methods of gene sequencing, such as with single-molecule-based sequencing utilizing arrays of single polynucleotide molecules (e.g., sequencing by synthesis (SBS)), have been disclosed as described in Patent Document 1 or Non-Patent Document 1, aimed at significant improvement in accuracy of gene expression analysis, as in the case of DNA microarray analysis. According to such technique, analyte polynucleotides modified with adequate primers are fixed to the substrate surface, and the resultant is used as a template to execute extension of each nucleotide with the use of a polymerase to construct complementary strands of the analyte polynucleotides. In each step of single-nucleotide extension, a fluorescent dye is introduced into the purine skeleton, the pyrimidine skeleton, or the end of a 3-phosphoric acid group, respectively, of each of the 4 different types of nucleotides. By conducting fluorescent detection in every step of extension for each single molecule, the nucleotide that has been introduced is distinguished. This step is repeated to decode the sequence of each single polynucleotide fixed site, and extensive analyte sequence information is obtained. In such a case, it is important to detect molecules with a high S/N ratio and improve the accuracy of sequencing. Since fluorescent information emitted from an enormous number of single polynucleotide fixed sites is detected with a CCD camara according to this technique, the average density for fixing polynucleotide molecules is determined in accordance with the pixel size of the CCD camera. Specifically, the average density for polynucleotide fixation or pixel resolution is regulated so as to capture a fluorescent signal from a single polynucleotide with a single pixel to as great an extent as possible. The pixel size is sub-micron (square) or greater when the spatial resolution of the optical detection system is taken into consideration.

In order to detect small quantities of DNA samples via sequencing as described above, it is necessary to improve the sensitivity of fluorescent detection. When fluorescent substances or luminescent substances that are not the targets of detection enter into the fluorescent detection region, fluorescence or luminescence emitted therefrom would be detected. When free fluorophores, impurities in a sample solution, or other substances adsorb to the planar surface of the evanescent field boundary in a non-specific manner, in particular, it would be difficult to distinguish fluorescence or luminescence emitted or light scattered from such non-specific absorptive materials from fluorescence or luminescence emitted from analytes. This may disadvantageously lower the fluorescent detection sensitivity or the accuracy of analysis. While such non-speicific absorptive materials can be avoided to some extent by coating a substrate surface or by other means, it is impossible to completely avoid such non-speicific absorptive materials. Thus, a method involving the use of technique for potentiation of fluorescence aimed at improvement in fluorescent detection sensitivity is reported in Non-Patent Document 2. In this case, silver nanoparticles resulting from modification of DNA probe molecules are fixed to a substrate and allowed to react with molecules in fluorescence-labeled analytes. When an excitation light is applied in order to detect the reaction amount, free electrons of the silver nanopartices cause local plasmon resonance, and fluorescence is potentiated. Sensitivity can be improved via such phenomena.

Fluorescence-enhanced fields are provided on the substrate in a grid-like manner at equal intervals, a single polymerase molecule is fixed to the fluorescence-enhanced field, and DNA is then subjected to extension. Since fluorescence excited by an evanescence is potentiated by the fluorescence-enhanced field, the S/N ratio or S/B ratio for fluorescent detection becomes sufficiently high even if non-specific adsorption takes place. However, variations occur in fine metal particle sizes, which may cause differences in the fluorescence potentiating effects among individual fine metal particles, and detection accuracy remains problematic. While a probe molecule is fixed to a fine metal particle by the liquid phase method, the site of fixation is determined at random. Thus, a probe molecule may be fixed to a region between a fine metal particle and the substrate, and it may inhibit extension by polymerase.

When fluorescence-enhanced fields are provided in a grid-like manner, a construct made of a noble metal is formed into the fluorescence-enhanced field via lithography. Thus, variations in fluorescence-enhanced fields may be reduced. In such a case, a probe molecule may be directly and selectively fixed to the fluorescence-enhanced field. Alternatively, a fluorescence-enhanced field and a metal sufrace having a composition different from that of the substrate may be provided as scaffolds for probe molecule fixation, and probe molecules may be selectively fixed. For example, Non-Patent Document 3 discloses a method of providing a metal oxide surface of $TiO_2$ at a position at which an avidin biomolecule is to be provided and forming a membrane for preventing non-specific adsorption on the other $SiO_2$ (quartz) surface. In such a case, introduction of a metal oxide surface of $TiO_2$ as a probe molecule scaffold is considered to make possible selective introduction of biomolecules into the fluorescence-enhanced field.

PRIOR ART DOCUMENTS

Patent Document

Patent Document 1: U.S. Pat. No. 6,787,308

Non-Patent Documents

Non-Patent Document 1: Proc. Natl. Acad. Sci., U.S.A., Vol. 100 (7), p. 3960, 2003
Non-Patent Document 2: Biochem. Biophys. Res. Comm., 306, p. 213, 2003
Non-Patent Document 3: Chem. Mater. 16, p. 5670, 2004

SUMMARY OF THE INVENTION

Objects to be Attained by the Invention

According to the method of Non-Patent Document 3, avidin is merely physically adsorbed, and its binding capacity is poor. When it is applied to a device, accordingly, it may be detached from the device during the process of extension or the like. Thus, it is necessary to fix the target DNA molecule via chemical binding. In general, avidin is fixed via specific binding with biotin, for example. In order to fix biotin via chemical binding, an amino group may be introduced into the fluorescence-enhanced field, and the amino group may be bound to a carboxyl group of biotin via coupling. When introduction of a compound having amino groups at the ends into the fluorescence-enhanced field is intended for the purpose of amino group introduction, however, the amino groups would disadvantageously adsorb to regions other than the fluorescence-enhanced field.

As described above, it was difficult to selectively introduce a scaffold for biomolecule fixation (which may be referred to as a "linker molecule") into a given region on the substrate when a biomolecule is selectively fixed to such region. Accordingly, it is an object of the present invention to provide a method of manufacturing a biomolecule modifying substrate that is capable of selectively fixing biomolecules to given regions thereon. In addition, it is another object of the present invention to provide a biomolecule modifying substrate manufactured by such method and comprising biomolecules selectively fixed to given regions.

Means for Attaining the Objects

The present invention, which has attained the above objects, includes the following.

(1) A biomolecule modifying substrate comprising:
a substrate at least comprising a first surface and a second surface;
a first linker molecule comprising a hydrocarbon chain and a functional group capable of selectively binding to the first surface at one end or in a side chain of the hydrocarbon chain, which is bound to the first surface via such functional group;
a second linker molecule comprising a reactive group capable of binding to the hydrocarbon chain of the first linker molecule, which is bound to the first linker molecule via a bond between the reactive group and the hydrocarbon chain; and
a biomolecule bound thereto via the second linker molecule.

(2) The biomolecule modifying substrate according to (1), wherein the first surface is made of a metal oxide and the second surface is made of a noble metal.

(3) The biomolecule modifying substrate according to (1), wherein the first surface is made of a metal oxide and the functional group capable of selectively binding to the first surface is a phosphate group and/or a silanol group.

(4) The biomolecule modifying substrate according to (1), wherein the first surface is a metal having a natural oxide film and the second surface is made of silicon dioxide or sapphire.

(5) The biomolecule modifying substrate according to (1), wherein the first surface is a metal having a natural oxide film and the functional group capable of selectively binding to the first surface is a phosphate group and/or a silanol group.

(6) The biomolecule modifying substrate according to (3) or (5), wherein the hydrocarbon chain of the first linker molecule has a phosphate group and/or silanol group at the end of an alkyl group represented by formula 1 and/or formula 2:

$$C_mH_{2m-1}PO_3H_2$$

$$C_mH_{2m-1}OPO_3H_2 \quad \text{(formula 1)}$$

$$C_mH_{2m-1}Si(X)_3 \quad \text{(formula 2)}$$

wherein m is an integer between 2 and 20, and at least 1 group represented by X is alkoxy or chlorine optionally containing methyl or ethyl.

(7) The biomolecule modifying substrate according to (3) or (5), wherein the hydrocarbon chain of the first linker molecule is a polymer chain comprising a phosphate group in the side chain of a compound represented by formula 3:

$$\text{(formula 3)}$$

wherein n is an integer of 1 or larger.

(8) The biomolecule modifying substrate according to (7), wherein the number average molecular weight of the polymer chain having a phosphate group is between 1,000 and 500,000.

(9) The biomolecule modifying substrate according to (1), wherein the first surface is made of a noble metal and the second surface is made of silicon dioxide.

(10) The biomolecule modifying substrate according to (1), wherein the first surface is made of a noble metal and the functional group capable of selectively binding to the first surface is a thiol group.

(11) The biomolecule modifying substrate according to (10), wherein the hydrocarbon chain of the first linker molecule has a thiol group at the end of an alkyl group of a compound represented by formula 4:

$$C_mH_{2m-1}SH \quad \text{(formula 4)}$$

wherein m is an integer between 2 and 20.

(12) The biomolecule modifying substrate according to (1), wherein the reactive group in the second linker molecule is a latent reactive group capable of binding to the hydrocarbon chain.

(13) The biomolecule modifying substrate according to (12), wherein the latent reactive group is at least 1 type of photoreactive compound selected from the group consisting of an anthrathione group, an anthraquinone group, a benzophenone group, an azide group, and a derivative of any thereof.

(14) The biomolecule modifying substrate according to (1), wherein the second linker molecule further comprises a reactive group capable of selectively binding to the biomolecule or a reactive group bound to the biomolecule.

(15) The biomolecule modifying substrate according to (1), wherein biotin contained in the second linker molecule is bound to biotin introduced into the biomolecule via avidin.

(16) A method of manufacturing a biomolecule modifying substrate comprising steps of:

bringing a first linker molecule comprising a hydrocarbon chain and a functional group capable of selectively binding to the first surface at one end or in a side chain of the hydrocarbon chain into contact with a substrate at least comprising the first surface and the second surface;

bringing a second linker molecule comprising a reactive group capable of binding to the hydrocarbon chain of the first linker molecule into contact at least with the first surface to which the first linker molecule has bound; and bringing a biomolecule into contact with to the first surface to bind the biomolecule thereto via the second linker molecule.

(17) The method of manufacturing a biomolecule modifying substrate according to (16), which further comprises a step of bringing an adsorption inhibitor molecule that inhibits biomolecule adsorption into contact with at least a region other than the first surface to which the second linker molecule has bound to form an adsorption inhibitor layer therein, following the step of bringing the second linker molecule into contact with the surface.

(18) The method of manufacturing a biomolecule modifying substrate according to (16), wherein the first surface is made of a metal oxide and the second surface is made of a noble metal.

(19) The method of manufacturing a biomolecule modifying substrate according to (16), wherein the first surface is made of a metal oxide and the functional group capable of selectively binding to the first surface is a phosphate group and/or silanol group.

(20) The method of manufacturing a biomolecule modifying substrate according to (16), wherein the first surface is a metal having a natural oxide film and the second surface is made of silicon dioxide or sapphire.

(21) The method of manufacturing a biomolecule modifying substrate according to (16), wherein the first surface is a metal having a natural oxide film and the functional group capable of selectively binding to the first surface is a phosphate group and/or silanol group.

(22) The method of manufacturing a biomolecule modifying substrate according to (19) or (21), wherein the hydrocarbon chain of the first linker molecule comprises a phosphate group and/or silanol group at the end of an alkyl group represented by formula 5 and/or formula 6:

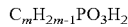

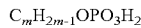 (formula 5)

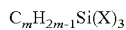 (formula 6)

wherein m is an integer between 2 and 20, and at least 1 group represented by X is alkoxy or chlorine optionally containing methyl or ethyl.

(23) The method of manufacturing a biomolecule modifying substrate according to (19) or (21), wherein the hydrocarbon chain of the first linker molecule is a polymer chain comprising a phosphate group in the side chain of a compound represented by formula 7:

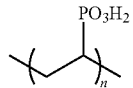 (formula 7)

wherein n is an integer.

(24) The method of manufacturing a biomolecule modifying substrate according to (23), wherein the number average molecular weight of the polymer chain comprising a phosphate group is between 1,000 and 500,000.

(25) The method of manufacturing a biomolecule modifying substrate according to (16), wherein the first surface is made of a noble metal and the second surface is made of silicon dioxide.

(26) The method of manufacturing a biomolecule modifying substrate according to (16), wherein the first surface is made of a noble metal and the functional group capable of selectively binding to the first surface is a thiol group.

(27) The method of manufacturing a biomolecule modifying substrate according to (26), wherein the hydrocarbon chain of the first linker molecule comprises a thiol group at the end of an alkyl group represented by formula 8:

 (formula 8)

wherein m is an integer between 2 and 20.

(28) The method of manufacturing a biomolecule modifying substrate according to (16), wherein the reactive group in the second linker molecule is a latent reactive group capable of binding to the hydrocarbon chain.

(29) The method of manufacturing a biomolecule modifying substrate according to (28), wherein the latent reactive group is at least 1 type of photoreactive compound selected from the group consisting of an anthrathione group, an anthraquinone group, a benzophenone group, an azide group, and a derivative of any thereof.

(30) The method of manufacturing a biomolecule modifying substrate according to (16), wherein the second linker molecule further comprises a reactive group capable of selectively binding to the biomolecule or a reactive group bound to the biomolecule.

(31) The method of manufacturing a biomolecule modifying substrate according to (16), wherein biotin contained in the second linker molecule is bound to biotin contained in the biomolecule via avidin.

This description includes part or all of the contents as disclosed in the description and/or drawings of Japanese Patent Application No. 2009-181743, which is a priority document of the present application.

Effects of the Invention

The biomolecule modifying substrate of the present invention comprises biomolecules selectively fixed in given regions thereon. This enables significant reduction in noise and the like caused by nonspecific adsorption of biomolecules or linker molecules used for fixing biomolecules. According to the method of manufacturing the biomolecule modifying substrate of the present invention, in addition, biomolecules can be fixed selectively in given regions on the substrate, and a biomolecule modifying substrate that is excellent in detection sensitivity or other properties can be manufactured.

EMBODIMENTS FOR CARRYING OUT THE INVENTION

Hereafter, the biomolecule modifying substrate and the method of manufacturing the same according to the present invention are described in detail with reference to the drawings.

Figure 1:
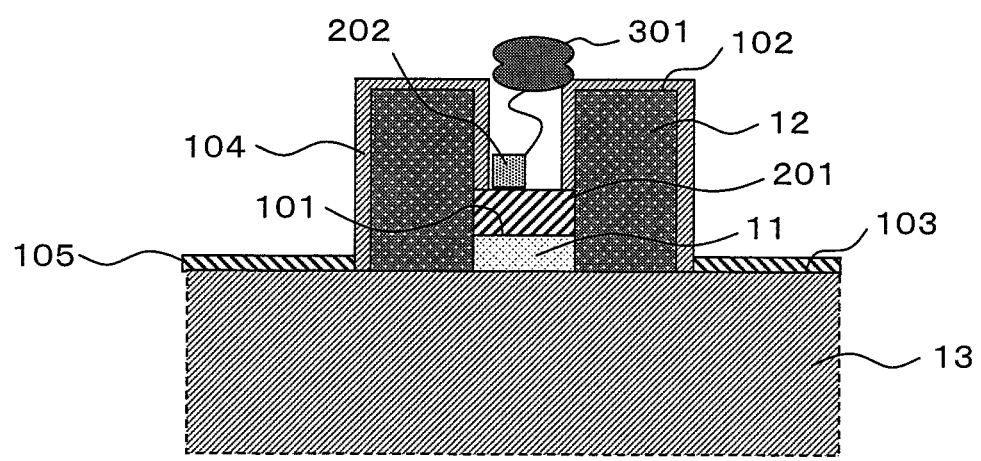
FIG. 1(a) and FIG. 1(b) are a plan view of a major part and a cross-sectional view of a major part, respectively, showing an embodiment of the biomolecule modifying substrate according to the present invention.
Figure 2:
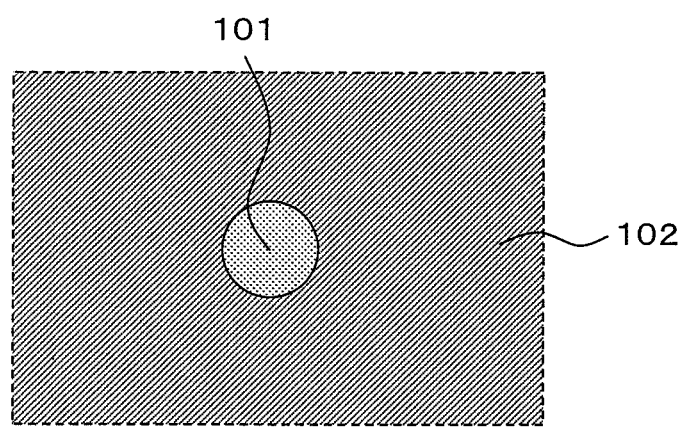
FIG. 2(a) and FIG. 2(b) are a plan view of a major part and a cross-sectional view of a major part, respectively, showing another embodiment of the biomolecule modifying substrate according to the present invention.
Figure 2:
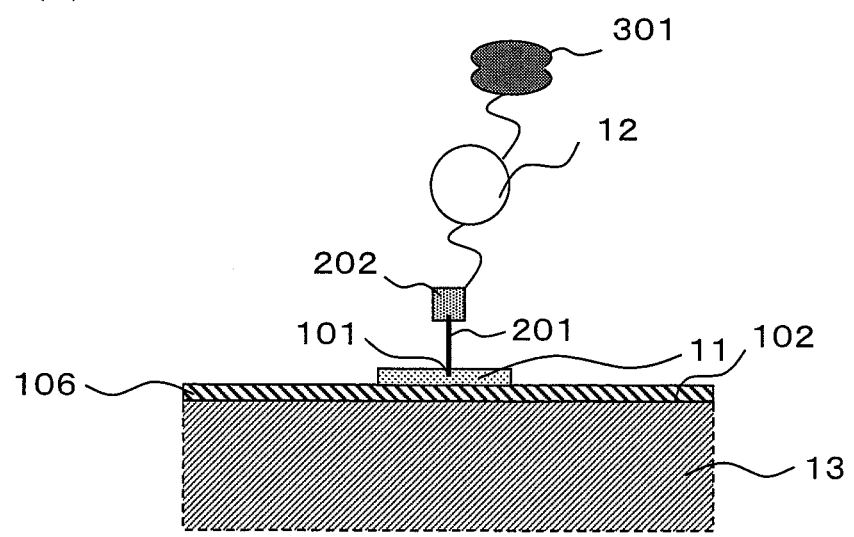
Figure 3:
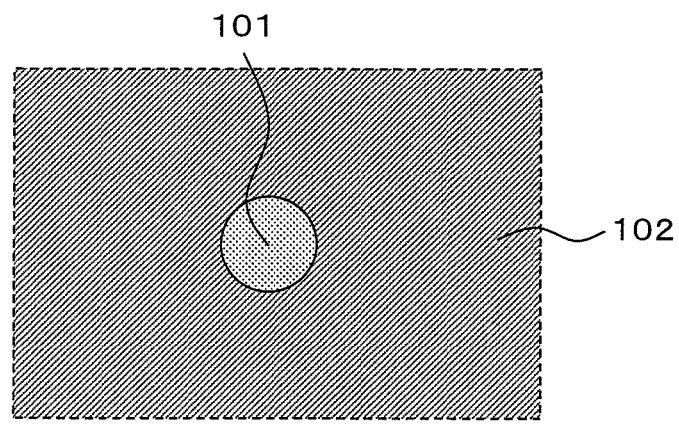
FIG. 3(a) and FIG. 3(b) are a plan view of a major part and a cross-sectional view of a major part, respectively, showing another embodiment of the biomolecule modifying substrate according to the present invention.
Figure 3:
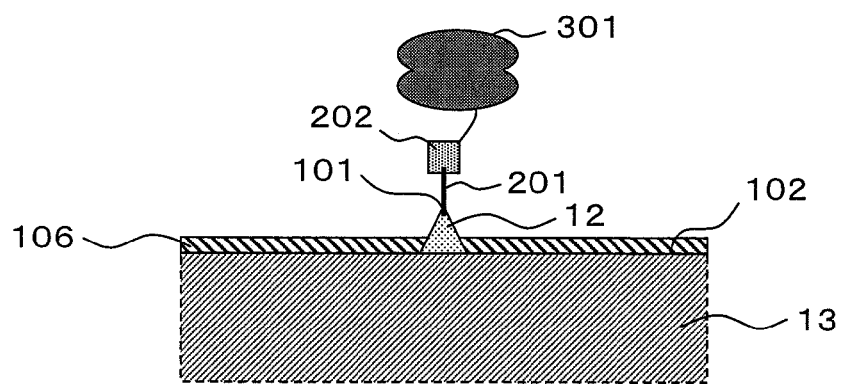

The biomolecule modifying substrate according to the present invention comprises a substrate 13 at least comprising the first surface 101 and the second surface 102 as shown in FIGS. 1 to 3, for example. The term "first surface 101" refers to a region to which a biomolecule is fixed via a linker molecule. The term "second surface 102" refers to a region to which a biomolecule is not fixed. Examples of biomolecules include, but are not particularly limited to, protein molecules, such as antibodies or enzymes.

The biomolecule modifying substrate according to the present invention comprises a compound layer 201 comprising a first linker molecule having a hydrocarbon chain and a functional group capable of selectively binding to the first surface 101 at one end or in a side chain of the hydrocarbon chain. The first linker molecule has at one of its ends a functional group and it is capable of binding a biomolecule to the first surface 101 via such functional group. The other end and the hydrocarbon chain of the first linker molecule may comprise a functional group as described above or a functional group different therefrom, provided that they would not inhibit the binding between the second linker molecule and the hydrocarbon chain described in detail below and provided that they would not bind to the second surface 102.

The compound layer 201 is provided selectively on the first surface 101, and it is not provided on regions other than the first surface 101, such as on the second surface 102. When the first surface 101 is composed of a metal oxide, such as TiO$_2$, Ta$_2$O$_5$, Al$_2$O$_3$, Nb$_2$O$_5$, or ZrO$_2$, for example, a phosphate group and/or a silanol group can be used as functional groups of the first linker molecule. When the first surface 101 is composed of a noble metal, such as Au, Ag, Cu, or Pt, for example, a thiol group can be used as a functional group of the first linker molecule. Thus, functional groups of the first linker molecule may be adequately selected in accordance with the material of the first surface 101, so that the compound layer 201 can be provided selectively on the first surface 101.

A hydrocarbon chain of the first linker molecule comprises, as a backbone, an alkyl group, such as an ethyl, propyl, butyl, pentyl, or hexyl group, an alkenyl group, or an alkynyl group, and it is not capable of adsorbing to the second surface 102. A hydrocarbon chain preferably has 2 to 20 carbon atoms, more preferably 5 to 15 carbon atoms, and further preferably 12 carbon atoms. The number of carbon atoms is not limited thereto, and a polymer compound having a long hydrocarbon chain may be used. When a polymer compound is used, the number average molecular weight is preferably 1,000 to 500,000, more preferably 5,000 to 200,000, and further preferably 10,000 to 100,000, although the number average molecular weight is not limited thereto. A hydrocarbon chain may comprise a functional group, such as a hydroxyl, phenyl, chloroalkyl, isocyanate, or epoxy group, corresponding to the backbone described above.

The biomolecule modifying substrate according to the present invention comprises a compound layer 202 comprising the second linker molecule having a reactive group capable of binding to the hydrocarbon chain of the first linker molecule. Examples of reactive groups capable of binding to the hydrocarbon chain of the first linker molecule that can be preferably used include latent reactive groups, such as photoreactive functional groups and thermochemically reactive functional groups. Use of photoreactive functional groups as reactive groups capable of binding to the hydrocarbon chain of the first linker molecule is particularly preferable. A compound having a photoreactive aryl ketone or azide group is preferably used as a photoreactive functional group, for example. Specific examples of photoreactive aryl ketone include, but are not limited to, an anthrathione group or a derivative thereof, an anthraquinone group or a derivative thereof, and a benzophenone group or a derivative thereof.

In addition, a biomolecule is directly or indirectly bound to the second linker molecule on the biomolecule modifying substrate according to the present invention. Specifically, the second linker molecule may have a structure comprising a reactive group capable of binding to the hydrocarbon chain of the first linker molecule introduced into a biomolecule. Alternatively, the second linker molecule may have a structure comprising an introduced reactive group capable of binding to a biomolecule or a reactive group introduced into the biomolecule. Examples of reactive groups capable of binding to biomolecules include, but are not particularly limited to, biotin, avidin, and epoxide. A functional group capable of complementarily binding to a biomolecule is further preferable. Examples include bonds resulting from interactions between a nucleic acid and a complementary nucleic acid, between a peptide nucleic acid and a nucleic acid, between an enzyme and a substrate, between a receptor and an effector, between lectin and sugar, between an antibody and an antigen, between avidin and biotin, and between streptoavidin and biotin. When a nucleic acid is to be fixed as a biomolecule, specifically, a complementary nucleic acid is introduced as a reactive group into the second linker molecule, for example. When an antibody is to be fixed as a biomolecule, for example, an antigen is introduced as a reactive group into the second linker molecule. When a protein is to be fixed as a biomolecule, for example, avidin is introduced into such protein molecule, and biotin is introduced as a reactive group into the second linker molecule. Alternatively, biotin may be introduced as a reactive group into the protein and the second linker molecule, and the protein may be bound to the second linker molecule via avidin.

The biomolecule modifying substrate shown in FIG. 1 comprises a biomolecule fixed thereto with the use of the first linker molecule and the second linker molecule, and it comprises a scaffold 11 and a fluorescence enhancer 12 sandwiching the scaffold 11 on the main surface of the substrate 13. The first surface 101 is the surface of the scaffold 11, and the second surface 102 is the surface of the fluorescence enhancer 12. The fluorescence enhancer 12 is capable of potentiating fluorescence generated in the vicinity of the first surface 101, and it is constructed in such a manner that a longitudinal cross-sectional area becomes smaller toward the first surface 101 in order to magnify the potentiating capacity.

Materials of the substrate 13 are not particularly limited, and any material that allows excitation light to be transmitted therethrough may be used. It is preferable that such material differ from that of the fluorescence enhancer 12 or scaffold 11. An adequate material for the substrate 13 may be selected in accordance with the purpose of use from among, for example, inorganic materials, such as glass or titania, semiconductor materials, such as silicon or GaAs, metals, such as copper, tantalum, or titanium, or organic materials, such as epoxy resin or polyimide.

A preferable material of the fluorescence enhancer 12 is a metal, metal alloy, or metal laminate. Examples of materials of the fluorescence enhancer 12 include Au, Pt, Ir, Pd, Ru, Ni, Ti, Sn, Ag, Cu, Rh, and Al. The structure of the fluorescence enhancer is not limited to the structure shown in the figure, as long as it is capable of potentiating light at the fluorescent wavelength to be detected. For example, it may be in a spherical form (e.g., a nanoparticle).

A material of the scaffold 11 is preferably different from that of the substrate 13 or fluorescence enhancer 12. Examples thereof include metal oxides, such as $TiO_2$, $Ta_2O_5$, $Al_2O_3$, $Nb_2O_5$, and $ZrO_2$. When Ti, Ni, Al, Sn, Pd, or the like is used for the fluorescence enhancer 12, alternatively, the material of the scaffold 11 may be a noble metal, such as Au, Ag, Cu, or Pt. The surface 11 may have an arbitrary thickness, and it is preferably between 0.1 nm and 10 nm from the viewpoint of evanescent wave transmission.

Figure 4:
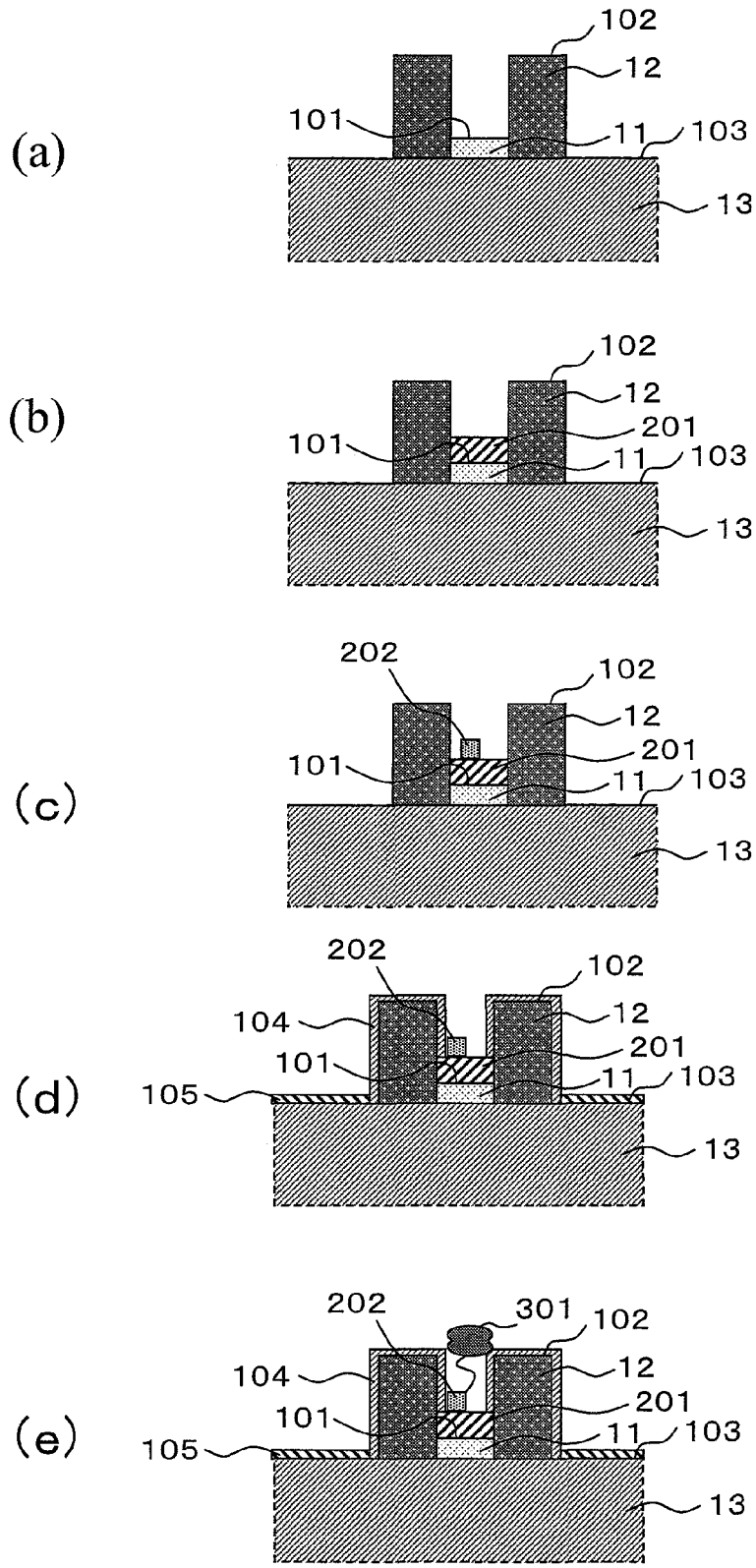
FIG. 4 is a flow chart showing the process of manufacturing the biomolecule modifying substrate shown in FIG. 1.

The biomolecule modifying substrate shown in FIG. 1 can be manufactured in accordance with a process flow shown in FIG. 4, for example. At the outset, the scaffold 11 and the fluorescence enhancer 12 are provided on the main surface of the substrate 13. The scaffold 11 and the fluorescence enhancer 12 can be manufactured to have desired configurations and dimensions via application of general thin-film formation and processing techniques. Subsequently, the construct is soaked in a solution containing the first linker molecule, the first linker molecule selectively binds to the surface of the scaffold 11 (the first surface 101) and the compound layer 201 is then formed on the scaffold 11 (FIG. 4(b)). The construct is then soaked in a solution containing the second linker molecule, the second linker molecule binds selectively to the first linker molecule, and the compound layer 202 is then formed (FIG. 4(c)). Alternatively, a solution containing the second linker molecule may be applied to the main surface of the construct to bind the first linker molecule to the second linker molecule. When a compound comprising a latent reactive group as the second linker molecule is used, electromagnetic waves or heat is provided, so that the latent reactive group becomes capable of binding to a hydrocarbon chain of the first linker molecule. Also, a compound in which the first linker molecule has bound to the second linker molecule in advance may be used to bind biomolecules to the scaffold 11. Subsequently, adsorption inhibitor molecules are fixed to the surface of the substrate 13 or fluorescence enhancer 12 to prevent nonspecific adsorption of biomolecules so as to form the adsorption inhibitor layers 104 and 105 (FIG. 4(d)). Thereafter, the biomolecules 301 are fixed via the second linker molecule (FIG. 4(e)). While the planar area of the scaffold 11 is preferably larger than the area that a single biomolecule 301 covers, it is preferably smaller than the area that two molecules cover.

Thus, a biomolecule modifying substrate comprising biomolecules selectively fixed to desired regions, such as the surface of the scaffold 11 (i.e., the first surface 101), can be manufactured. Since the biomolecule modifying substrate according to the present invention is capable of selectively introducing the first linker molecules onto the first surface 101, in particular, biomolecules can be prevented from being fixed to other regions, such as the fluorescence enhancer 12 or substrate 13. An amino group contained in aminopropylphosphonic acid adsorbs to a metal oxide surface (e.g., $TiO_2$), a noble metal surface (e.g., Au), or an inorganic material surface (e.g., $SiO_2$). When aminopropylphosphonic acid that has been used as a linker molecule to fix a biomolecule in the past is applied to the construct as shown in FIG. 1, accordingly, biomolecules would become fixed to the surface of the fluorescence enhancer 12 or substrate 13. In such a case, detection of various reactions involving the use of biomolecules with the use of fluorescence leads such reactions to proceed on the surface of the fluorescence enhancer 12 or substrate 13, the reactions cause noise, and lowered detection sensitivity becomes a serious issue of concern. However, the biomolecule modifying substrate according to the present invention is capable of fixing biomolecules selectively to the surface of the scaffold 11 (i.e., the first surface 101), noise generation can be avoided, and excellent detection sensitivity can be realized.

The biomolecule modifying substrate shown in FIG. 1 comprises biomolecules fixed thereto with the use of the first linker molecule and the second linker molecule, and it comprises a scaffold 11 and a fluorescence enhancer 12 sandwiching the scaffold 11 on the main surface of the substrate 13. The first surface 101 is the surface of the scaffold 11, and the second surface 102 is the surface of the fluorescence enhancer 12. The fluorescence enhancer 12 is capable of potentiating fluorescence generated on the first surface 101, and it is constructed in such a manner that a longitudinal cross-sectional area becomes smaller toward the first surface 101 in order to magnify such potentiating capacity.

Materials of the substrate 13 are not particularly limited, and any material that allows excitation light to be transmitted therethrough may be used. It is preferable that such material differ from that of the fluorescence enhancer 12 or scaffold 11. An adequate material for the substrate 13 may be selected in accordance with the purpose of use from among, for example, inorganic materials, such as glass or titania, semiconductor materials, such as silicon or GaAs, metals, such as copper, tantalum, or titanium, or organic materials, such as epoxy resin or polyimide.

A preferable material of the fluorescence enhancer 12 is a metal, metal alloy, or metal laminate. Examples of materials of the fluorescence enhancer 12 include Au, Pt, Ir, Pd, Ru, Ni, Ti, Sn, Ag, Cu, Rh, and Al. The structure of the fluorescence enhancer is not limited to the structure shown in the figure, as long as it is capable of potentiating light at the fluorescent wavelength to be detected. For example, it may be in a spherical form (e.g., a nanoparticle).

A material of the scaffold 11 is preferably different from that of the substrate 13 or fluorescence enhancer 12. Examples thereof include metal oxides, such as $TiO_2$, $Ta_2O_5$, $Al_2O_3$, $Nb_2O_5$, and $ZrO_2$. When Ti, Ni, Al, Sn, or Pd is used for the fluorescence enhancer 12, alternatively, the material of the scaffold 11 may be a noble metal, such as Au, Ag, Cu, or Pt. The surface 11 may have an arbitrary thickness, and it is preferably between 0.1 nm and 10 nm from the viewpoint of evanescent wave transmission. Accordingly, use of a compound into which a phosphate group capable of selectively binding to a metal oxide, such as $TiO_2$, $Ta_2O_5$, $Al_2O_3$, $Nb_2O_5$, or $ZrO_2$, has been introduced as the first linker molecule is preferable for the biomolecule modifying substrate shown in FIG. 1.

The biomolecule modifying substrate shown in FIG. 2 comprises biomolecules fixed thereto with the use of the first linker molecule and the second linker molecule. It comprises a circular scaffold 11 on the main surface of the substrate 13 and fine particles such as those of the fluorescence enhancer 12. The fluorescence enhancer 12 is bound thereto via the second linker molecule, and the biomolecules 301 are fixed to the surface thereof. The first surface 101 is the surface of the circular scaffold 11, and the second surface 102 is the surface 102 of the substrate 13. The fluorescence enhancer 12 is composed of fine particles capable of potentiating fluorescence generated in the vicinity.

An adequate material for the substrate 13 may be selected in accordance with the purpose of use from among, for example, inorganic materials, such as glass or titania, semiconductor materials, such as silicon or GaAs, metals, such as copper, tantalum, or titanium, or organic materials, such as epoxy resin or polyimide.

Preferable examples of fine particles of the fluorescence enhancer 12 include, but are not limited to, nanoparticles of a noble metal, such as Au, Pt, or Ag. Alternatively, semiconductor compounds, such as CdSe or CdS, may be used.

A material of the scaffold 11 is preferably different from that of the substrate 13. Examples thereof that can be used include metals such as Ti, Ta, Al, Nb, and Zr. In such a case, the surface 101 is a natural oxide film, such as $TiO_2$, $Ta_2O_5$, $Al_2O_3$, $Nb_2O_5$, or $ZrO_2$, and the first linker molecule capable of binding to the surface 101 may be used. Alternatively, a metal oxide, such as $TiO_2$, $Ta_2O_5$, $Al_2O_3$, $Nb_2O_5$, or $ZrO_2$, may be used. A noble metal, such as Au, Ag, Cu, or Pt, may be used. The scaffold 11 may have an arbitrary thickness, and it is preferably between 0.1 nm and 10 nm in view of evanescent wave transmission. When the surface 101 is made of a metal oxide, such as $TiO_2$, $Ta_2O_5$, $Al_2O_3$, $Nb_2O_5$, or $ZrO_2$, accordingly, use of a compound into which a phosphate group capable of selectively binding to a metal oxide, such as $TiO_2$, $Ta_2O_5$, $Al_2O_3$, $Nb_2O_5$, or $ZrO_2$, has been introduced as the first linker molecule is preferable. When the surface 101 is composed of a noble metal or metal, such as Au, Pt, Ir, Pd, Ru, Ni, Ti, Sn, Ag, Cu, Rh, or Al, use of a compound into which a thiol group capable of binding to a noble metal or metal, such as Au, Pt, Ir, Pd, Ru, Ni, Ti, Sn, Ag, Cu, Rh, or Al, has been introduced is preferable.

Figure 5:
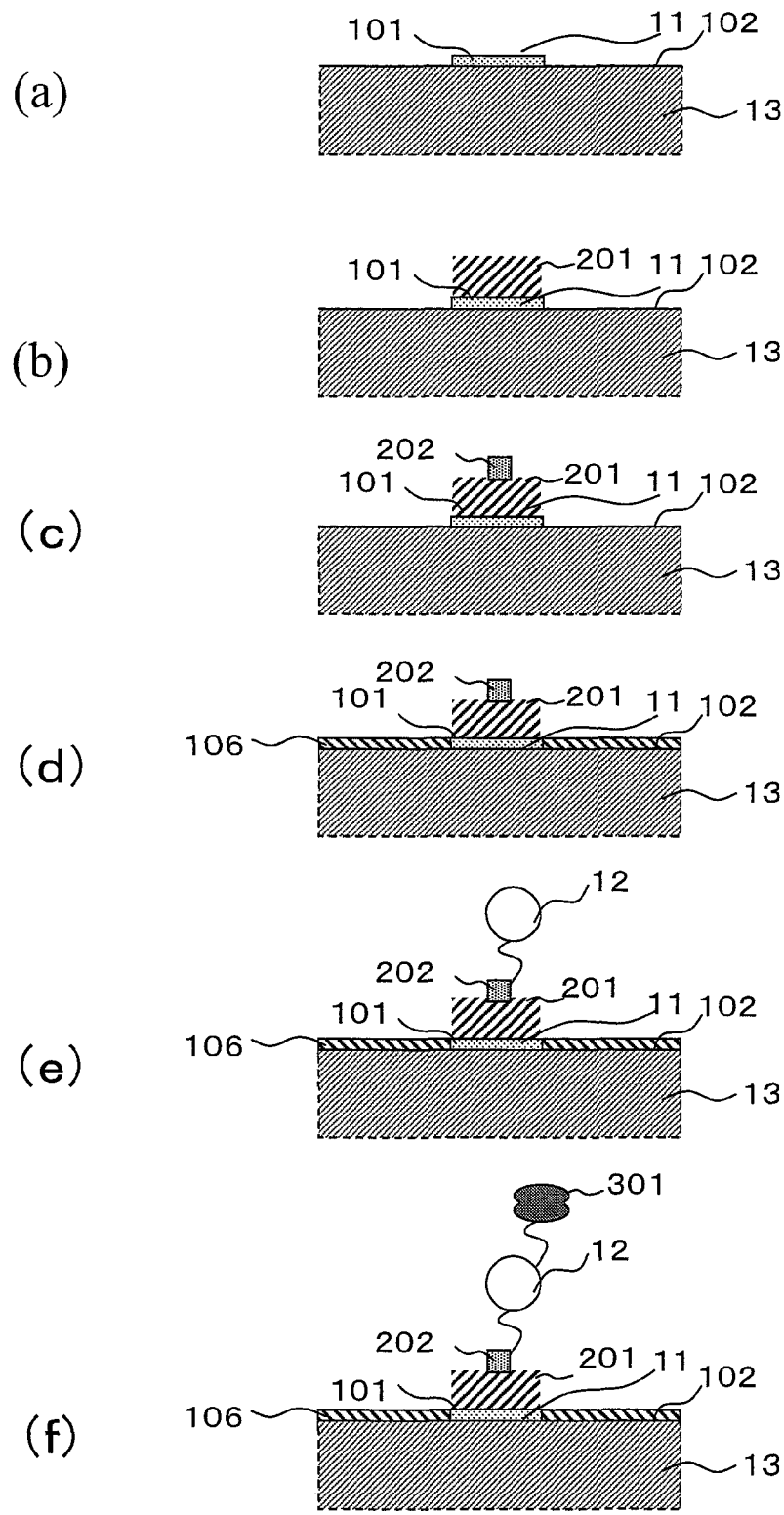
FIG. 5 is a flow chart showing the process of manufacturing the biomolecule modifying substrate shown in FIG. 2.

FIG. 5 shows a flow chart illustrating the process for manufacturing the biomolecule modifying substrate shown in FIG. 2. At the outset, a scaffold 11 in an approximately circular shape is provided on the main surface of the substrate 13 (FIG. 5(a)). The scaffold 11 in an approximately circular shape can be manufactured via conventional thin-film formation and processing techniques. Subsequently, this construct is soaked in a solution containing the first linker molecule, and the first linker molecule is selectively introduced into the top of the scaffold 11 (FIG. 5(b)). In this case, the first linker molecule selectively binds to the surface of the scaffold 11, and it does not adsorb to the surface of the substrate 13. When the construct is soaked in a solution containing the second linker molecule, the second linker molecule selectively binds to the first linker molecule (FIG. 5(c)). The first linker molecule may be bound to the second linker molecule by coating the main surface of the construct with a solution containing the second linker molecule. When a compound containing a latent reactive group as the second linker molecule is used, electromagnetic waves or heat is provided, so that the latent reactive group becomes capable of binding to a hydrocarbon chain of the first linker molecule. Also, a compound in which the first linker molecule has bound to the second linker molecule in advance may be used to bind biomolecules to the scaffold 11. Subsequently, adsorption inhibitor molecules are fixed to the surface of the substrate 13 to prevent nonspecific adsorption of biomolecules and form an adsorption inhibitor layer 106 (FIG. 5(d)). Thereafter, fine particles of the fluorescence-enhanced field 12 are fixed via the second linker molecule (FIG. 5(e)). Further, the biomolecules 301 are fixed via the fluorescence-enhanced field 12 (FIG. 5(f)). The planar area of the scaffold 11 in an approximately circular shape is preferably smaller than the area that a single biomolecule 301 covers.

Thus, a biomolecule modifying substrate comprising biomolecules selectively fixed to desired regions, such as the surface of the scaffold 11 in an approximately circular shape (i.e., the first surface 101), can be manufactured. Since the biomolecule modifying substrate according to the present invention is capable of selectively introducing the first linker molecules onto the first surface 101, in particular, biomolecules can be prevented from being fixed to other regions, such as the surface of the substrate 13. As with the case of the biomolecule modifying substrate shown in FIG. 1, accordingly, the biomolecule modifying substrate shown in FIG. 2 is capable of fixing biomolecules selectively to the first surface 101, noise generation can be avoided, and excellent detection sensitivity can be realized.

In contrast, the biomolecule modifying substrate shown in FIG. 3 comprises biomolecules fixed thereto with the use of the first linker molecule and the second linker molecule, and it comprises the fluorescence enhancer 12 in an approximately conical shape on the main surface of the substrate 13. The first surface 101 described above is a surface on the top of the fluorescence enhancer 12 in an approximately conical shape and the second surface 102 is a surface of the substrate 13. The fluorescence enhancer 12 is capable of potentiating fluorescence generated at the top (i.e., the first surface 101), and it is constructed in such a manner that a lateral cross-sectional area becomes smaller toward the first surface 101 in order to magnify such potentiating capacity. FIG. 2 shows an example of the biomolecule modifying substrate comprising biomolecules fixed to the fluorescence enhancer 12. Accordingly, use of the biomolecule modifying substrate shown in FIG. 3 comprising a compound into which a thiol group capable of selectively binding to a noble metal or metal, such as Au, Pt, Ir, Pd, Ru, Ni, Ti, Sn, Ag, Cu, Rh, or Al, has been introduced as the first linker molecule is preferable.

Figure 6:
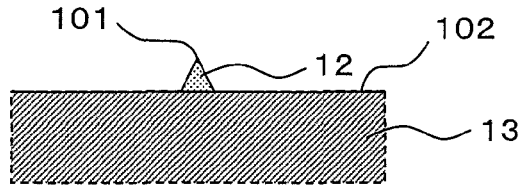
FIG. 6 is a flow chart showing the process of manufacturing the biomolecule modifying substrate shown in FIG. 3.
Figure 6:
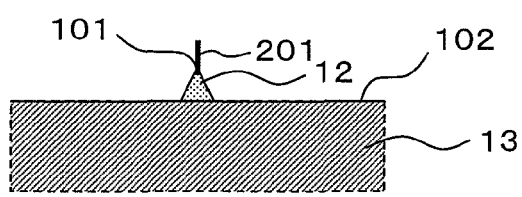
Figure 6:
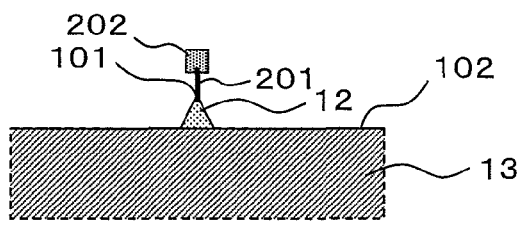
Figure 6:
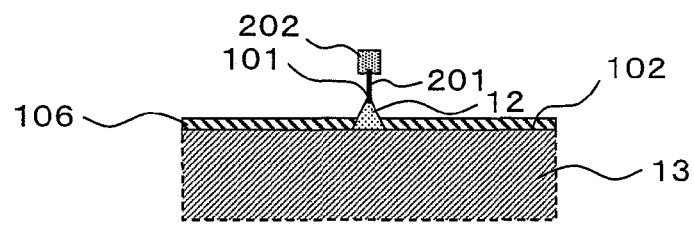
Figure 6:
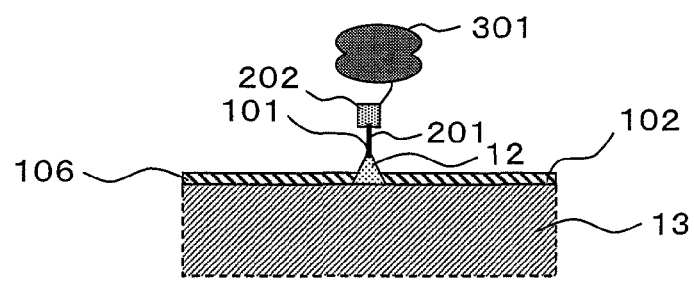

FIG. 6 shows a flow chart illustrating the process for manufacturing the biomolecule modifying substrate shown in FIG. 3. At the outset, the fluorescence enhancer 12 in an approximately conical shape is provided on the main surface of the substrate 13 (FIG. 6(a)). The fluorescence enhancer 12 in an approximately conical shape can be manufactured via conventional thin-film formation and processing techniques. Subsequently, this construct is soaked in a solution containing the first linker molecule, and the first linker molecule is selectively introduced into the top of the fluorescence enhancer 12 (FIG. 6(b)). In this case, the first linker molecule selectively binds to the surface of the top of the fluorescence enhancer 12, and it does not adsorb to the surface of the substrate 13. When the construct is soaked in a solution containing the second linker molecule, the second linker molecule selectively binds to the first linker molecule (FIG. 6(c)). The first linker molecule may be bound to the second linker molecule by coating the main surface of the construct with a solution containing the second linker molecule. When a compound containing a latent reactive group as the second linker molecule is used, electromagnetic waves or heat is provided, so that the latent reactive group becomes capable of binding to a hydrocarbon chain of the first linker molecule. Also, a compound in which the first linker molecule has bound to the second linker molecule in advance may be used to bind biomolecules to the scaffold 11. Subsequently, adsorption inhibitor molecules are fixed to the surface of the substrate 13 to prevent nonspecific adsorption of biomolecules and form an adsorption inhibitor layer 106 (FIG. 6(d)). Thereafter, the biomolecules 301 are fixed via the second linker molecule (FIG. 6(e)). Also, it is preferable that the planar area at the top of the fluorescence enhancer 12 in an approximately conical shape be smaller than the area that a single biomolecule 301 covers.

Thus, a biomolecule modifying substrate comprising biomolecules selectively fixed to desired regions, such as the surface on the top of the fluorescence enhancer 12 in an approximately conical shape (i.e., the first surface 101), can be manufactured. Since the biomolecule modifying substrate according to the present invention is capable of selectively introducing the first linker molecules onto the first surface 101, in particular, biomolecules can be prevented from being fixed to other regions, such as the surface of the substrate 13. As with the case of the biomolecule modifying substrates shown in FIGS. 1 and 2, accordingly, the biomolecule modifying substrate shown in FIG. 3 allows biomolecules to be fixed selectively to the first surface 101, noise generation to be avoided, and excellent detection sensitivity to be realized.

It is particularly preferable that the biomolecule modifying substrates shown in FIGS. 1, 2, and 3 each comprise a single type of biomolecule fixed to a region of interest (i.e., the first surface 101). Fixation of DNA polymerase as a single type of biomolecule, for example, is suitable for single-molecule-based sequencing (sequencing by synthesis (SBS)). That is, nucleic acid synthesis caused by a single DNA polymerase is employed with the use of a fluorescence-labeled nucleotide as a substrate, and fluorescence detection is carried out for each single nucleotide extension using a given nucleic acid fragment as a template. Thus, the sequence of the template nucleic acid can be determined With the use of the biomolecule modifying substrate according to the present invention, in particular, DNA polymerase can be selectively and securely fixed to a given region, and noise generated in a region other than the reaction field can be prevented.

EXAMPLES

Hereafter, the present invention is described in greater detail with reference to the examples, although the technical scope of the present invention is not limited thereto.

Example 1

In Example 1, the present invention is described with reference to adequate comparative examples. At the outset, a biomolecule modifying substrate having the constitution as shown in FIG. 1 provided with Au as the fluorescence enhancer 12, $TiO_2$ as the scaffold 11, and $SiO_2$ as the substrate 13 is manufactured, biomolecules are selectively introduced onto these three types of surfaces, and the results thereof are described.

(Preparation of Substrate)

At the outset, three types of substrate surfaces; i.e., Au, $TiO_2$, and $SiO_2$ surfaces, were prepared. An Au film and a $TiO_2$ film were formed on the $SiO_2$ substrate via sputtering. The Au or $TiO_2$ film thickness was approximately 10 nm. Synthetic quartz was used for an $SiO_2$ substrate. The substrate surface was washed via reactive ion etching (RIE) with oxygen gas. At the same time, a hydroxyl group was introduced. RIE was carried out using an ICP dry etching apparatus. RIE was carried out at an output power of 100 W, an oxygen gas pressure of 1 Pa, and a gas flow rate of 10 $cm^3$/min for 60 to 180 seconds.

(Surface Processing of Substrate)

Alkyl phosphate having an alkyl chain and a phosphate group to be bound to $TiO_2$ was used as the first linker molecule. As alkyl phosphate, specifically, 1-dodecylphosphonic acid having 12 carbon chains was used (see the structural formula below). While alkyl phosphate having 12 carbon chains was used in this example, a polymer chain such as poly(vinyl phosphonic acid) may be used to bind a phosphate group to $TiO_2$.

(formula 9)

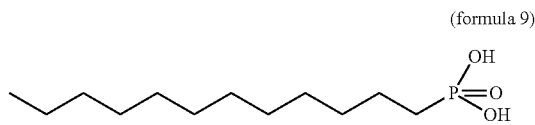 [SMILES: CCCCCCCCCCCCP(=O)(O)O]

Hereafter, the method of substrate processing is described. Specifically, the $SiO_2$ substrate comprising the Au film and $TiO_2$ film was soaked in a solution of 1-dodecylphosphonic acid in a mixed solvent of heptane/isopropanol (v/v=99.5/0.5) for 48 hours. Thereafter, the substrate was washed with isopropanol, and the amount of phosphorus adsorbed to the substrate surface was then quantified via X-ray photoelectron spectroscopy (XPS) in order to evaluate the surface conditions of the substrate.

As a result of determination of the amounts of phosphorus adsorbed to the substrate surface via XPS before and after processing with 1-dodecylphosphonic acid, the integrated intensities of P 2P-derived peaks of the Au film, the $TiO_2$ film, and the $SiO_2$ substrate were found to be 0 cps, 530 cps, and 100 cps, respectively.

In addition, the substrate processed with 1-dodecylphosphonic acid was coated with biotin-dPEG3™-benzophenone (IRIS Biotech; see the structural formula below) as the second linker molecule with the use of a spin coater, and ultraviolet light (wavelength: 365 nm) was applied for 30 minutes to bind benzophenone to an alkyl group on the substrate. While a compound having a benzophenone group was used as the second linker in this example, photobiotin having an azide group may be used.

In this example, the substrate was processed with 1-dodecylphosphonic acid as the first linker, and biotin-dPEG3™-benzophenone was then allowed to bind to 1-dodecylphosphonic acid as the second linker, although processing is not particularly limited thereto. Alternatively, 1-dodecylphosphonic acid may be allowed to bind to biotin-dPEG3™-benzophenone in advance, followed by purification, and the substrate may then be processed with the 1-dodecylphosphonic acid to which biotin-dPEG3™-benzophenone has bound.

(formula 10)

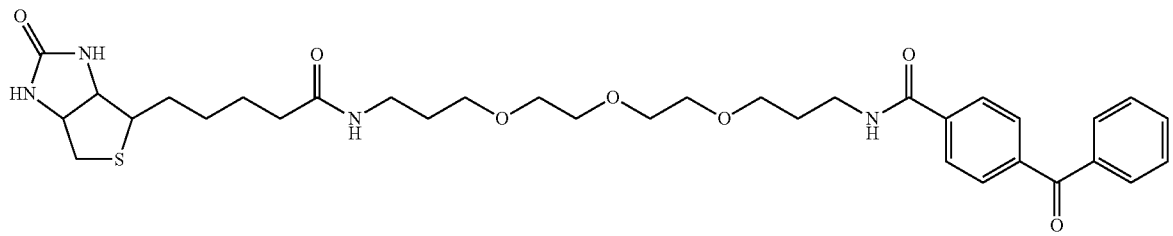

(Biomolecule Binding)

Figure 7:
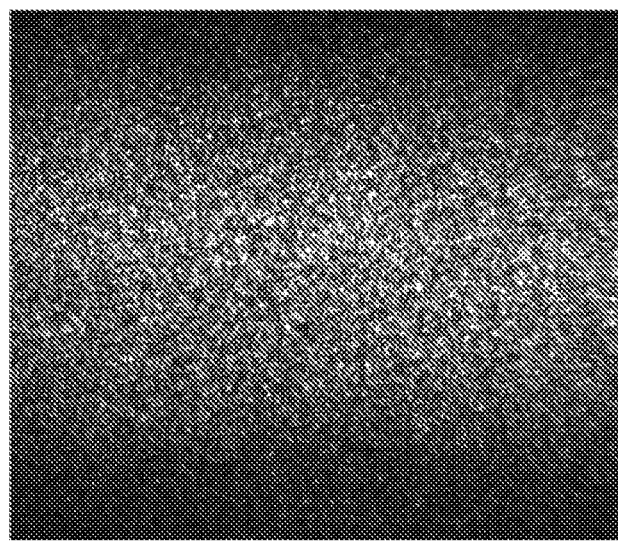
FIG. 7(a) is a photograph showing the results of fluorescent observation of the TiO$_2$ film surface on the SiO$_2$ substrate and FIG. 7(b) is a photograph showing the results of fluorescent observation of the surface of the TiO$_2$ substrate and the Au film surface on the SiO$_2$ substrate.
Figure 7:

Alexa Fluor® 532, which is a fluorescent dye having streptavidin, was dissolved in a weakly basic carbonate buffer, and the SiO$_2$ substrate having an Au film and a TiO$_2$ film was soaked therein. Thus, biotin in the second linker molecule introduced onto the substrate surface was allowed to bind to streptavidin contained in the fluorescent dye to fix the fluorescent dye on the substrate. Thereafter, the substrate was washed with ultrapure water to remove excessive Alexa Fluor 532. Fluorescence on the surface of the SiO$_2$ substrate having an Au film and a TiO$_2$ film was observed and the number of fluorescence-derived luminescent spots was counted. The results are shown in FIG. 7. FIG. 7(a) shows the results of photographing the surface of the TiO$_2$ film on the SiO$_2$ substrate and FIG. 7(b) shows the results of photographing the surface of the SiO$_2$ substrate and the surface of the Au film on the SiO$_2$ substrate. As is apparent from FIG. 7(a), luminescent spots were observed in the observation area on the TiO$_2$ film at a density of 1 luminescent spot/μm$^2$ or greater. In contrast, luminescent spots were observed on the SiO$_2$ substrate surface and the Au film surface at a density of 0.1 luminescent spots/μm$^2$ or less, as is apparent from FIG. 7(b). The results indicate that the first linker molecule and the second linker molecule can be selectively introduced onto the TiO$_2$ film surface without being introduced onto either the SiO$_2$ substrate or Au film surface, and that a fluorescent dye can be selectively fixed to the TiO$_2$ film surface.

Example 2

In Example 2, the biomolecule modifying substrate having the constitution as shown in FIG. 2 provided with the fluorescence enhancer 12 coated with Au, the scaffold 11 coated with TiO$_2$, and the substrate 13 coated with SiO$_2$ is provided as with the case of Example 1, biomolecules are selectively introduced onto these three types of surfaces, and the results thereof are described.

(Preparation of Substrate)

At the outset, three types of substrate surfaces; i.e., Au, TiO$_2$, and SiO$_2$ surfaces, were prepared. An Au film and a TiO$_2$ film were formed on the SiO$_2$ substrate via sputtering. The Au or TiO$_2$ film thickness was approximately 10 nm. Synthetic quartz was used for an SiO$_2$ substrate. The substrate surface was washed via reactive ion etching (RIE) with oxygen gas. At the same time, a hydroxyl group was introduced. RIE was carried out using an ICP dry etching apparatus. RIE was carried out at an output power of 100 W, an oxygen gas pressure of 1 Pa, and a gas flow rate of 10 cm$^3$/min for 60 to 180 seconds.

(Surface Processing of Substrate)

Poly(vinyl phosphonic acid) comprising an alkyl chain as a main chain and a phosphate group to be bound to TiO$_2$ in the side chain was used as the first linker molecule. Specifically, poly(vinyl phosphonic acid) having a molecular weight of 24,000 was used (see the structural formula below). While poly(vinyl phosphonic acid) having a molecular weight of 24,000 was used in this example, poly(vinyl phosphonic acid) with a larger or smaller molecular weight may be used without particular limitation.

(formula 11)

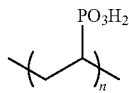

Hereafter, the method of processing the substrate is described. Specifically, poly(vinyl phosphonic acid) was dissolved in ultrapure water to a concentration of 2 wt % therein, and the SiO$_2$ substrate having an Au film and a TiO$_2$ film was soaked in the resulting aqueous solution at 90° C. for 5 minutes. Thereafter, the substrate was washed with ultrapure water, and the amount of phosphorus adsorbed to the substrate surface was then quantified via X-ray photoelectron spectroscopy (XPS) in order to evaluate the surface conditions of the substrate.

As a result of determination of the amounts of phosphorus adsorbed to the substrate surface via XPS before and after processing with poly(vinyl phosphonic acid), the integrated intensities of P 2P-derived peaks of the Au film, the TiO$_2$ film, and the SiO$_2$ substrate were found to be 460 cps, 1500 cps, and 0 cps, respectively.

In addition, the substrate processed with poly(vinyl phosphonic acid) was coated with EZ-Link TFPA-PEG$_3$-Biotin (Thermo-Pierce; see the structural formula below), which is photobiotin having an azide group, as the second linker molecule with the use of a spin coater, and ultraviolet light (wavelength: 365 nm) was applied for 30 minutes to bind benzophenone to an alkyl group on the substrate. While a compound having an azide group was used as the second linker in this example, a biotin compound having a benzophenone group may be used.

In this example, the substrate was processed with poly (vinyl phosphonic acid) as the first linker, and photobiotin was then allowed to bind to poly(vinyl phosphonic acid) as the second linker, although processing is not particularly limited thereto. Alternatively, poly(vinyl phosphonic acid) may be allowed to bind to photobiotin in advance, followed by purification, and the substrate may then be processed with poly(vinyl phosphonic acid) to which photobiotin has bound.

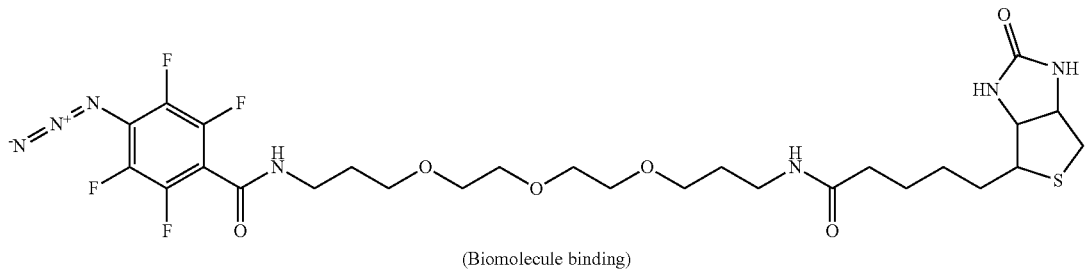

(formula 12)

(Biomolecule binding)

Figure 8:
FIG. 8(a) is a photograph showing the results of fluorescent observation of the TiO$_2$ film surface on the SiO$_2$ substrate and FIG. 8(b) is a photograph showing the results of fluorescent observation of the surface of the TiO$_2$ substrate and the Au film surface on the SiO$_2$ substrate.
Figure 8:
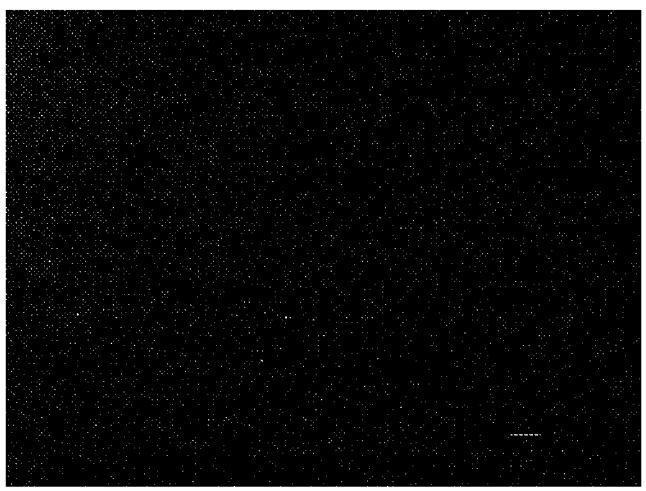

In the same manner as in Example 1, Alexa Fluor® 532, which is a fluorescent dye having streptavidin, was dissolved in a weakly basic carbonate buffer, and the $SiO_2$ substrate having an Au film and a $TiO_2$ film was soaked therein. Thus, biotin in the second linker molecule introduced onto the substrate surface was allowed to bind to streptavidin contained in the fluorescent dye to fix the fluorescent dye to the substrate. Thereafter, the substrate was washed with ultrapure water to remove excessive Alexa Fluor 532. Fluorescence on the surface of the $SiO_2$ substrate having an Au film and a $TiO_2$ film was observed, and the number of fluorescence-derived luminescent spots was counted. The results are shown in FIG. 8. FIG. 8(a) shows the results of photographing the surface of the $TiO_2$ film on the $SiO_2$ substrate and FIG. 8(b) shows the results of photographing the surface of the $SiO_2$ substrate and the surface of the Au film on the $SiO_2$ substrate. As is apparent from FIG. 8(a), luminescent spots were observed in the observation area on the $TiO_2$ film at a density of 1 luminescent spot/$\mu m^2$ or greater. In contrast, luminescent spots were observed on the surface of the $SiO_2$ substrate and that of the Au film at a density of only 0.1 luminescent spots/$\mu m^2$ or less, as is apparent from FIG. 8(b). The results indicate that the first linker molecule and the second linker molecule can be selectively introduced onto the surface of the $TiO_2$ film without being introduced onto the surface of the $SiO_2$ substrate or Au film, and a fluorescent dye can be selectively fixed to the surface of the $TiO_2$ film.

Comparative Example 1

In Comparative Example 1, the first linker molecule was introduced onto the $SiO_2$ substrate having an Au film and a $TiO_2$ film in the same manner as in Example 1, except that aminoalkylphosphonic acid having an amino group and a phosphate group to be bound to $TiO_2$ at the ends was used as the first linker molecule. In Comparative Example 1, specifically, 3-aminopropylphosphonic acid having 3 carbon chains was used as aminoalkylphosphonic acid. 3-aminopropylphosphonic acid was dissolved in ultrapure water, and the $SiO_2$ substrate having an Au film and a $TiO_2$ film was soaked in the resulting solution for 48 hours. Thereafter, the substrate was washed with ultrapure water, and the amount of phosphorus adsorbed to the substrate surface was then quantified via X-ray photoelectron spectroscopy (XPS) in order to evaluate the surface conditions of the substrate.

As a result of determination of the amounts of phosphorus adsorbed to the substrate surface via XPS before and after processing with 3-aminopropylphosphonic acid, the integrated intensities of P 2P-derived peaks of the Au film, the $TiO_2$ film, and the $SiO_2$ substrate were found to be 140 cps, 640 cps, and 270 cps, respectively. That is, the first linker molecule used in Comparative Example 1 comprises an amino group in part of its molecular structure, which makes it impossible for biomolecules to selectively bind to the $TiO_2$ film, and binding of biomolecules to the surface of the Au film or $SiO_2$ substrate is observed. In such a case, biomolecules may be fixed via the first linker molecule, so that biomolecules may also be fixed to the surface of the Au film or $SiO_2$ substrate.

INDUSTRIAL APPLICABILITY

The present invention can be applied to a substrate on which biomolecules, such as proteins or nucleic acids, are fixed. Since the present invention is characterized by biomolecule fixation, the present invention can be applied to various conventional substrates or the like (e.g., DNA microarrays or protein chips).

All publications, patents, and patent applications cited herein are incorporated herein by reference in their entirety.

DESCRIPTION OF NUMERICAL REFERENCES

11: scaffold; 12: fluorescence enhancer; 13: substrate; 101: first surface; 102: second surface; 201 and 202: compound layers; 301: biomolecule

The invention claimed is:
1. A biomolecule modifying substrate comprising:
 a substrate;
 a first surface on the substrate, the first surface comprising a metal oxide;
 a second surface on the substrate, the second surface comprising a noble metal;
 a first linker molecule comprising a hydrocarbon chain and a functional group at one end or in a side chain of the hydrocarbon chain, the functional group capable of selectively binding to the first surface, the first linker molecule bound to the first surface via the functional group;
 a second linker molecule comprising biotin and a reactive group, the reactive group capable of binding to the hydrocarbon chain of the first linker molecule, the second linker molecule bound to the first linker molecule via a bond between the reactive group and the hydrocarbon chain;
 a biomolecule comprising an introduced biotin; and
 an avidin,
 wherein the biotin contained in the second linker molecule is bound to the biotin introduced into the biomolecule via the avidin, and
 wherein the functional group of the first linker molecule capable of selectively binding to the first surface is a phosphate group.

2. The biomolecule modifying substrate according to claim 1, wherein the first surface is a metal having a natural oxide film.

3. The biomolecule modifying substrate according to claim 1, wherein the hydrocarbon chain of the first linker molecule comprises an alkyl group and is represented by the formula selected from the group consisting of $C_mH_{2m-1}PO_3H_2$, $C_mH_{2m-1}OPO_3H_2$, wherein m is an integer between 2 and 20.

4. The biomolecule modifying substrate according to claim 1, wherein the hydrocarbon chain of the first linker molecule is a polymer chain comprising a phosphate group in the side chain of a compound represented by formula 3:

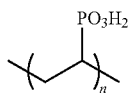

(formula 3)

wherein n is an integer of 1 or larger.

5. The biomolecule modifying substrate according to claim 1, wherein the reactive group in the second linker molecule is a latent reactive group capable of binding to the hydrocarbon chain and the latent reactive group is at least 1 type of photoreactive compound selected from the group consisting of an anthrathione group, an anthraquinone group, a benzophenone group, an azide group, and a derivative of any thereof.

6. The biomolecule modifying substrate according to claim 1, wherein the second linker molecule further comprises a reactive group capable of selectively binding to the biomolecule or a reactive group bound to the biomolecule.

7. The biomolecule modifying substrate according to claim 1,
wherein the first linker molecule lacks a functional group inhibiting binding between the second linker molecule and the hydrocarbon chain of the first linker molecule, and
wherein the first linker molecule lacks a functional group capable of binding to the second surface.

8. The biomolecule modifying substrate according to claim 1,
wherein the hydrocarbon chain of the first linker molecule comprises an alkyl group, and
wherein functional group of the second linker molecule is bonded to the alkyl group of the first linker molecule.

* * * * *